United States Patent [19]

Stelpflug et al.

[11] Patent Number: 5,602,316
[45] Date of Patent: Feb. 11, 1997

[54] INBRED CORN LINE ZS1783

[75] Inventors: Richard G. Stelpflug, Slater; Mark J. Messmer, Ankeny, both of Iowa

[73] Assignee: Zenco (No 4) Limited, London, England

[21] Appl. No.: 413,204

[22] Filed: Mar. 28, 1995

[51] Int. Cl.⁶ ............................... A01H 5/00; A01H 4/00; A01H 1/00; C12N 5/04
[52] U.S. Cl. ................. 800/200; 800/250; 800/DIG. 56; 435/412; 47/58
[58] Field of Search ..................................... 800/200, 205, 800/250, DIG. 56; 47/58; 435/240.4, 45, 49, 50

[56] References Cited

PUBLICATIONS

Cole, E. H. and M. G. Neuffer. The Genetics of Corn, p. 111.
Conger, B. V., F. J. Novak, R. Afza, and K. Erdelsky. "Somatic embryogenesis from cultured leaf segments of *Zea mays*", Plant Cell Reports, 6:345–347 (1987).
Duncan, D. R., M. E. Williams, B. E. Zehr and J. M. Widholm. "The production of callus capable of plant regeneration from immature embryos of numerous *Zea mays* genotypes", Planta, 165:322–332 (1985).
Edallo, et al., "Chromosomal Variation and Frequency of Spontaneous Mutation Associated with in Vitro Culture and Plant Regeneration in Maize" Maydica XXVI, pp. 39–56 (1981).
Forsberg, R. A. and R. R. Smith. "Sources, Maintenance, and Utilization of Parental Material", Hybridization of Crop Plants, Chapter 4, pp. 65–81 (1980).
Green, C. E. and R. L. Phillips. "Plant Regeration from Tissue Cultures of Maize", Crop Science, vol. 15, pp. 417–421 (1975).
Green, C. E. and C. A. Rhodes. "Plant Regeneration in Tissue Cultures of Maize", Maize for Biological Research, pp. 367–372 (1982).
Hallauer, et al, "Corn Breeding", Corn and Corn Improvement pp. 463–564 (1988). Sprague et al, eds.
Lowe, Keith. Patent Application 0 160 390.
Meghji, M. R., J. W. Dudley, R. J. Lambert, and G. F. Sprague. "Inbreeding Depression, Inbred and Hybrid Grain Yields, and Other Traits of Maize Genotypes Representing Three Eras". Crop Science, vol. 24, pp. 545–549 (1984).
Phillips, et al., "Cell/Tissue Culture and In Vitro Manipulation", In Corn & Corn Improvement, 3rd Ed., ASA Publication, #18, pp. 345–349 & 356–357 (1988).
Poehlman, John Milton. *Breeding Field Crop*, AVI Publishing Company, Inc., Westport, Connecticut, pp. 237–246 (1987).
Rao, K. V., et al., "Somatic Embryogenesis in Glume Callus Cultures", Osmania University, Hyberabad, India.
Sass (1977) "Morphology". In Corn & Corn Improvement. ASA Publication. Madison, WI, pp. 89–109.
Songstad, David D., David R. Duncan, and Jack M. Widholm. "Effect of 1–aminocyclopropane–1–carboxylic acid, silver nitrate, and norbornadiene on plant regeneration from maize callus cultures", Plant Cell Reports, 7:262–265 (1988).
Tomes, et al, "the Effect of Parental Genotype on Initiation of Embryogenic Callus from Elite Maize (*Zea mays* 1.) Germplasm". Theor. Appl. Genet. 70., pp. 505–509. (1985).
Troyer, et al., "Selection for Early Flowering in Corn: 10 Late Synthetics". Crop Science, vol. 25, pp. 695–697 (1985).
Umbeck, et al. "Reversion of Male–Sterile T–Cytoplasm Maize to Male Fertility in Tissue Culture", Crop Science vol. 23, pp. 584–588 (1983).
Wright, H., "Commercial Hybrid Seed Production", Hybridization of Crop Plants, pp. 161–176, (1980).
Wych, R. D., "Production of Hybrid Seed Corn"; Corn and Corn Improvement, pp. 565–607 (1988).

*Primary Examiner*—Gary Benzion
*Attorney, Agent, or Firm*—Dana Rewoldt

[57] ABSTRACT

Broadly this invention provides inbred corn line ZS1783. The methods for producing a corn plant by crossing the inbred line ZS1783 are encompassed by the invention. Additionally, the invention relates to the various parts of inbred ZS1783 including culturable cells. This invention relates to hybrid corn seeds and plants produced by crossing the inbred line ZS1783 with at least one other corn line.

11 Claims, No Drawings

INBRED CORN LINE ZS1783

FIELD OF THE INVENTION

This invention is in the field of corn breeding, specifically relating to an inbred corn line designated ZS1783.

BACKGROUND OF THE INVENTION

The original maize plant was indigenous to the Western Hemisphere. The plants were weedlike and only through the efforts of early breeders was a cultivated crop species developed. The physical traits of maize are such that self pollination or cross pollination can occur. Each plant has a separate male and female flower, the tassel and ear, respectively. Natural pollination occurs when wind transfers pollen from tassel to the silks on the corn ears. This type of pollination contributed to the wide variation of maize varieties present in the Western Hemisphere.

The development of a planned breeding program for maize only occurred in the last century. Originally, maize was an open pollinated variety having heterogeneous genotypes. The maize farmer selected uniform ears from the yield of these genotypes and reserved them for planting the next season. The result was a field of maize plants that are segregating for a variety of traits. This type of maize selection lead to at most incremental increases in seed yield.

Large increases in seed yield were the result of the development of hybrid corn varieties in planned breeding programs. Hybrids were developed by selecting corn lines and selfing these lines for several generations to develop homozygous pure inbred lines and crossing selected inbred lines with unrelated inbred lines to produce hybrid progeny (F1). Inbred lines can be difficult to produce since the inbreeding process in corn decreases the vigor. However, when two inbred lines are crossed, the hybrid plant evidences greatly increased vigor compared to open pollinated segregating maize plants. An important factor of the homozygosity and the homogeneity of the inbred lines is that the hybrid from any cross will always be the same, and can be reproduced.

The ultimate objective of the commercial maize seed companies is to produce high yielding, agronomically sound plants which perform well in certain regions or areas of the Corn Belt. To produce these types of hybrids, the companies must develop inbreds which carry needed traits into the hybrid combination. Hybrids are not uniformly adapted for the Corn Belt, but are specifically adapted for regions of the Corn Belt. Northern regions of the Corn Belt require shorter season hybrids than do southern regions of the Corn Belt. Hybrids that grow well in Colorado and Nebraska soils may not flourish in rich Illinois soil. Thus, a variety of major agronomic traits are important in hybrid combination for the various Corn Belt regions, and have an impact on hybrid performance.

Inbred line development and hybrid testing have been emphasized in the past half century in commercial maize production as a means to increase hybrid performance. Inbred development is usually done by pedigree selection. Pedigree selection can be selection in an F2 population produced from a planned cross of two genotypes (often elite inbred lines), or selection of progeny of synthetic varieties, open pollinated, composite, or backcross populations. This type of selection is effective for highly inheritable traits, but other traits, for example, yield requires replicated test. crosses at a variety of stages for accurate selection.

Maize breeders select for a variety of traits in inbreds that impact hybrid performance along with selecting for acceptable parental traits. Such traits include yield potential in hybrid combination; dry down; maturity; grain moisture at harvest; greensnap; resistance to root lodging; resistance to stalk lodging; grain quality; disease and insect resistance; ear and plant height; performance in different soil types such as: low level of organic matter, clay, sand, black, high pH, low pH; performance in: wet environments, drought environments, and no tillage conditions. These traits appear to be governed by a complex genetic system that makes selection and breeding of an inbred line extremely difficult. Even if an inbred in hybrid combination has excellent yield (a desired characteristic), it may not be useful because it fails to have acceptable parental traits such as seed yield, seed size, pollen production, good silks, plant height, etc.

To illustrate the difficulty of breeding and developing inbred lines, the following example is given. Two inbreds compared for similarity of 29 traits differed significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. Selection of the specific inbred combination is also influenced by the specific selection environment on many of these 18 traits which makes the probability of obtaining this one inbred even more remote. Thus, the general procedure of producing a non segregating $F_1$ generation and self pollinating to produce a $F_2$ generation that segregates for traits does not easily lead to a useful inbred. Great care and breeder expertise must be used in selection of breeding material to continue to increase yield and agronomics of inbreds and resultant commercial hybrids.

SUMMARY OF THE INVENTION

The present invention relates to an inbred corn line ZS1783. Specifically, this invention relates to plants and seeds of this line. Additionally, this relates to a method of producing hybrid seed corn from this inbred. More particularly, this invention relates to the unique combination of traits that combine in corn line ZS1783.

Generally then, broadly the present invention includes an inbred corn seed designated ZS1783. This seed produces a corn plant.

The invention also includes the tissue culture of regenerable cells of ZS1783 wherein the tissue regenerates plants having the genotype of ZS1783. The tissue culture is selected from the group consisting of leaves, pollen, embryos, roots, root tips, anthers, silk, flowers, kernels, ears, cobs, husks and stalks, and cells and protoplasts thereof. The corn plant regenerated from ZS1783 having ZS1783's genotype.

The invention extends to hybrid seed produced by planting, in pollinating proximity, seeds of corn inbred lines ZS1783 and another inbred line; cultivating corn plants resulting from said planting; preventing pollen production by the plants of one of the inbred lines; allowing natural cross pollinating to occur between said inbred lines; and harvesting seeds produced on plants of the inbred. The hybrid seed produced by hybrid combination of plants of inbred corn seed designated ZS1783 and plants of another inbred line. Hybrid plants grown from this hybrid seed.

The invention further includes a method of hybrid F1 production. A first generation (F1) hybrid corn plant produced by the process of planting, in pollinating proximity, seeds of corn inbred lines ZS1783 and another inbred line; cultivating corn plants resulting from said planting; preventing pollen production by the plants of one of the inbred lines; allowing natural cross pollinating to occur between said inbred lines; harvesting seeds produced on plants of the inbred; and growing a harvested seed.

A tissue culture of the regenerable cells of hybrid plants produced with use of ZS1783 genetic material. A tissue culture of the regenerable cells of the corn plant produced by the method described above.

DEFINITIONS

In the description and examples which follow, a number of terms are used. In order to provide a clear and consistent understanding of the specifications and claims, including the scope to be given such terms, the following definitions are provided.

BL MOIST

The moisture percentage of the grain at black layer, i.e., when 50% of the plants per plot have reached physiological maturity.

COLD GERM

Cold Germ is a measurement of seed germination under cold soil conditions. Data is reported as percent of seed germinating.

ECB

European corn borer a maize eating insect. ECBI is the first brood generation of European corn borers. ECBII is the second generation of European corn borers.

EMERGE

The number of emerged plants per plot (planted at the same seedling rate) collected when plants have two fully developed leaves.

GI

This is a selection index which provides a single quantitative measure of the worth of a hybrid based on four traits. Yield is the primary trait contributing to index values. The GI value is calculated by combining stalk lodging, root lodging, yield and dropped ears according to the attached mathematical formula:

$$GI = 100 + 0.5(YLD) - 0.9 (\%STALK\ LODGE) - 0.9 (\%ROOT\ LODGE) - 2.7 (\%DROPPED\ EAR)$$

GLS

Grey Leaf Spot (*Cercospora Zeae*) disease rating. This is rated on a 1–9 scale with a "1" being very susceptible, and a "9" being-very resistant.*

* Resistant—on a scale of 1–9 with 9 evidencing the trail most strongly: 1–2.9 ratings are susceptible, 3–5.9 ratings are intermediate, and 6–9 ratings are resistant.

GW Goss Wilt (*Corynebacterium nebraskense*). This is rated on a 1–9 scale with a "1" being very susceptible, and a "9" being very resistant. *

HEATP10

The number of Growing Degree Units (GDU's) or heat units required for an inbred line or hybrid to have approximately 10 percent of the plants shedding pollen. This trait is measured from the time of planting. Growing Degree Units are calculated by the Barger Method where the GDU's for a 24 hour period are:

$$GDU = \frac{(Max\ Temp\ (°F.) + Min\ Temp\ (°F.))}{2} - 50$$

The highest maximum temperature used is 86° F. and the lowest minimum temperature used is 50° F. For each inbred or hybrid it takes a certain number of GDU's to reach various stages of plant development.

HEATBL

The number of GDU's after planting when approximately 50 percent of the inbred or hybrid plants in a plot have grain which has reached physiological maturity (black layer).

HEATPEEK

The number of GDU's after planting of an inbred when approximately 50 percent of the plants show visible tassel extension.

HEATP50

The number of GDU's required for an inbred or hybrid to have approximately 50 percent of the plants shedding pollen. Growing Degree Units are calculated by the Barger Method as shown in the HEATP10 definition.

HEATP90

The number of GDU's accumulated from planting when the last 100 percent of plants in an inbred or hybrid are still shedding enough viable pollen for pollination to occur. Growing Degree Units are calculated by the Barger Method as shown in the HEATP10 definition.

HEATS10

The number of GDU's required for an inbred or hybrid to have approximately 10 percent of the plants with silk emergence of at least 0.5 inches. Growing Degree Units are calculated by the Barger Method as shown in the HEATP10 definition.

HEATS50

The number of GDU's required for an inbred or hybrid to have approximately 50 percent of the plants with silk emergence of at least 0.5 inches. Growing Degree Units are calculated by the Barger Method as shown in the HEATP10 definition.

HEATS90

The number of GDU's required for an inbred or hybrid to have approximately 90 percent of the plants with silk emergence of at least 0.5 inches. Growing Degree Units are calculated by the Barger Method as shown in the HEATP10 definition.

$MDMV_A$

Maize Dwarf Mosaic Virus strain A. The cord is rated on a 1–9 scale with a "1" being very susceptible, and a "9" being very resistant.*

* Resistant—on a scale of 1–9 with 9 evidencing the trail most strongly: 1–2.9 ratings are susceptible, 3–5.9 ratings are intermediate, and 6–9 ratings are resistant.

$MDMV_B$

Maize Dwarf Mosaic Virus strain B. This is rated on a 1–9 scale with a "1" being very susceptible and a "9" being very resistant.*

* Resistant—on a scale of 1–9 with 9 evidencing the trail most strongly: 1–2.9 ratings are susceptible, 3–5.9 ratings are intermediate, and 6–9 ratings are resistant.

MOISTURE

The average percentage grain moisture of an inbred or hybrid at harvest time.

NLB

Northern Leaf Blight (*Exserohilum turcicum*) disease rating. This is rated on a 1–9 scale with a "1" being very susceptible, and a "9" being very resistant.*

* Resistant—on a scale of 1–9 with 9 evidencing the trail most strongly: 1–2.9 ratings are susceptible, 3–5.9 ratings are intermediate, and 6–9 ratings are resistant.

PCT TILLER

The total number of tillers per plot divided by the total number of plants per plot.

PLANT

This term includes plant cells, plant protoplasts, plant cell tissue cultures from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

PLANT HEIGHT

The distance in centimeters from ground level to the base of the tassel peduncle.

RM

Predicted relative maturity based on the moisture percentage of the grain at harvest. This rating is based on known set of checks and utilizes standard linear regression analyses and is referred to as the Minnesota Relative Maturity Rating System.

SHED

The volume of pollen shed by the male flower rated on a 1–9 scale where a "1" is a very light pollen shedder, a "4.5" is a moderate shedder, and a "9" is a very heavy shedder. If the Table(s) 3 have reduced the 1–9 shed scale to a 1–3 shed scale then any shed on Table 3 can be multiplied by 3 to reach the 1–9 shed scale.

SLB

Southern Leaf Blight (*Bipolaris maydis*) disease rating. This is rated on a 1–9 scale with a "1" being very susceptible, and a "9" being very resistant.*

* Resistant—on a scale of 1–9 with 9 evidencing the trail most strongly: 1–2.9 ratings are susceptible, 3–5.9 ratings are intermediate, and 6–9 ratings are resistant.

TWT

The measure of the weight of grain in pounds for a one bushel volume adjusted for percent grain moisture.

VIGOR

Visual rating of 1 to 9 made 2–3 weeks post-emergence where a "1" indicates very poor early plant development, and a "9" indicates superior plant development.

WARM GERM

A measurement of seed germination under ideal (warm, moist) conditions. Data is reported as percent of seeds germinating.

YIELD (YLD)

Actual yield of grain at harvest adjusted to 15.5% moisture. Measurements are reported in bushels per acre.

% DROPPED EARS (DE)

The number of plants per plot which dropped their primary ear divided by the total number of plants per plot.

% LRG FLAT

Percentage by weight of shelled corn that passes through a $^{26}/_{64}$ inch round screen and a $^{14}/_{64}$ inch slot screen, but does not pass through a screen with $^{20.5}/_{64}$ inch round openings.

% LRG ROUND

Percentage by weight of shelled corn that passes through a $^{26}/_{64}$ inch round screen, but does not pass through a $^{14}/_{64}$ inch slot screen or a screen with $^{20.5}/_{64}$ inch round openings.

% MED FLAT

Percentage by weight of shelled corn that passes through a $^{20.5}/_{64}$ inch round screen and a $^{13}/_{64}$ inch slotted screen, but does not pass through a screen with $^{17}/_{64}$ inch round openings.

% MED ROUND

Percentage by weight of shelled corn that passes through a $^{20.5}/_{64}$ inch round screen, but does not pass through a $^{13}/_{64}$ inch slot screen or a screen with $^{17}/_{64}$ inch round openings.

% SML FLAT

Percentage by weight of shelled corn that passes through a $^{17}/_{64}$ inch round screen and a $^{12}/_{64}$ inch slotted screen, but does not pass through a screen with $^{15}/_{64}$ inch round openings.

% SML ROUND

Percentage by weight of shelled corn that passes through a $^{17}/_{64}$ inch round screen, but does not pass through a $^{12}/_{64}$ inch slotted screen or a screen with $^{15}/_{64}$ inch round openings.

% ROOT LODGE (RL)

Percentage of plants per plot leaning more that 30 degrees from vertical divided by total plants per plot.

% STALK LODGE (SL)

Percentage of plants per plot with the stalk broken below the primary ear node divided by the total plants per plot.

* Resistant—on a scale of 1–9 with 9 evidencing the trait most strongly: 1–2.9 ratings are susceptible, 3–5.9 ratings are intermediate, and 6–9 ratings are resistant.

DETAILED DESCRIPTION OF THE INVENTION

ZS1783 can be used as a female or a male line due to its pollen shed and seed production abilities. This ZS1783 line evidences good to excellent emergence. Additionally, ZS1783 has a broad area of adaptation, good general combining ability, and specific combining ability with above average root lodging resistance.

The inbred has shown uniformity and stability within the limits of environmental influence for all the traits as descried in the Variety Description Information (Table 1) that follows. Most of the data in the Variety Description information was collected at Slater, Iowa.

The inbred has been self-pollinated for a sufficient number of generations to give inbred uniformity. During plant selection in each generation, the uniformity of plant type was selected to ensure homozygosity and phenotypic stability. The line has been increased in isolated farmland environments with data on uniformity and agronomic traits being observed to assure uniformity and stability. No variant traits have been observed or are expected in ZS1783.

The best method of producing the invention, ZS1783 which is substantially homozygous, is by planting the seed of ZS1783 which is substantially homozygous and self-pollinating or sib pollinating the resultant plant in an isolated environment, and harvesting the resultant seed or the resultant pollen.

TABLE 1

INBRED ZS1783

ZS1783
VARIETY DESCRIPTION INFORMATION
1  Type: Dent
2  Region Best Adapted: North central from east to west

#3 MATURITY

| DAYS | HEATUNITS | |
|---|---|---|
| 84 | 1589 | FROM PLANTING TO 50% OF PLANTS IN SILK |
| 83 | 1577 | FROM PLANTING TO 50% OF PLANTS IN POLLEN |
| 7 |  | FROM 10% TO 90% POLLEN SHED |

#4 PLANT DATA

| 4 | ANTHOCYANIN OF BRACE ROOTS: 1 = ABSENT 2 = FAINT 3 = MODERATE 4 = DARK |
|---|---|

#5 LEAF COLOR/DATA

| 3/DARK GREEN | LEAF COLOR **MUNSELL CODE-5GY 3/4 |
|---|---|
| 6 | LEAF SHEATH PUBESCENCE (1 = NONE TO 9 = PEACH FUZZ) |
| 4 | MARGINAL WAVES (1 = NONE TO 9 = MANY) |
| 5 | LONGITUDINAL CREASES (1 = NONE TO 9 = MANY) |

#6 TASSEL COLOR/DATA

| 5 | POLLEN SHED (0 = STERILE TO 9 = HEAVY SHEDDER) |
|---|---|
| 5/GREEN-YELLOW | ANOTHER COLOR **MUNSELL CODE-5Y 8/8 (GREEN TINT) |
| 2 | GLUME COLOR **MUNSELL CODE-5GY 6/6 |
| 2 | BAR GLUME: 1 = ABSENT 2 = PRESENT |

#7A EAR (UNHUSKED DATA) COLOR/DATA

| 7/YELLOW | SILK COLOR (3 DAYS AFTER EMERGE) **MUNSELL CODE-5Y 8/4 |
|---|---|
| 1/LIGHT GREEN | FRESH HUSK (25 DAYS AFTER 50% SILK) **MUNSELL CODE-2.5GY 6/6 |
| 22/TAN | DRY HUSK COLOR (65 DAYS AFTER 50% SILK **MUNSELL CODE-2.5Y 8/2 |
| 1 | POSITION OF EAR AT DRY HUSK: 1 = UPRIGHT 2 = HORIZONTAL 3 = PENDENT |
| 5 | HUSK TIGHTNESS (1 = VERY LOOSE TO 9 = VERY TIGHT) |
| 2 | HUSK EXTENSION AT HARVEST: 1 = EXPOSED EAR 2 = 8 CM 3 = 8–10 CM 4 = >10 CM |

#7B EAR (HUSKED DATA) DATA

| 1 | KERNEL ROWS: 1 = INDISTINCT 2 = DISTINCT |
|---|---|
| 1 | ROW ALIGNMENT: 1 = STRAIT 2 = SLIGHT CURVE 3 = SPIRAL |
| 2 | EAR TAPPER: 1 = STRAIT 2 = AVERAGE 3 = EXTREME |

#8 KERNEL (DRY) COLOR/DATA

| 1 | ALEURONE COLOR PATTERN: 1 = HOMO 2 = SEG |
|---|---|
| 8/YELLOW-ORANGE | ALEURONE COLOR **MUNSELL CODE-5Y 8/12 |
| 8/YELLOW-ORANGE | HARD ENDOSPERM COLOR **MUNSELL CODE-2.5Y 7/10 |
| 3 | ENDOSPERM TYPE |
| 7/YELLOW | CROWN COLOR **MUNSELL CODE-2.5Y 8/10 |

#9 COB COLOR

| 14/RED | COB COLOR **MUNSELL CODE-10R 5/10 |
|---|---|

COLOR CHOICES (Use in conjunction with Munsell color code to describe all color choices

| 01 = Light Green | 06 = Pale Yellow | 11 = Pink | 16 = Pale Purple | 21 = Buff |
|---|---|---|---|---|
| 02 = Medium Green | 07 = Yellow | 12 = Light Red | 17 = Purple | 22 = Tan |
| 03 = Dark Green | 08 = Yellow-Orange | 13 = Cherry Red | 18 = Colorless | 23 = Brown |
| 04 = Very Dark Green | 09 = Salmon | 14 = Red | 19 = White | 24 = Bronze |
| 05 = Green-Yellow | 10 = Pink-Orange | 15 = Red & White | 20 = White Capped | 25 = Variegated (Describe) |
| | | | | 26 = Other (Describe) |

| #10 | N | MEAN | STD | T-STAT | PROB | 95% CI |
|---|---|---|---|---|---|---|
| EAR HEIGHT(CM) | 15 | 64.87 | 6.12 | 41.07 | 0.0000 | (61.77,67.96) |
| LENGTH OF PRIMARY EAR LEAF(CM) | 15 | 84.20 | 5.03 | 64.81 | 0.0000 | (81.65,86.75) |
| WIDTH OF PRIMARY EAR LEAF(CM) | 15 | 7.87 | 0.40 | 76.28 | 0.0000 | (7.66,8.07) |
| TOP EAR INTERNODE(CM) | 15 | 12.93 | 0.94 | 53.15 | 0.0000 | (12.46,13.41) |
| DEGREE OF LEAF ANGLE | 15 | 32.40 | 2.10 | 59.82 | 0.0000 | (31.34,33.46) |
| # OF EARS PER PLANT | 15 | 1.13 | 0.35 | 12.47 | 0.0000 | (0.96,1.31) |
| # OF LEAVES ABOVE TOP EAR | 15 | 4.67 | 0.49 | 37.04 | 0.0000 | (4.42,4.91) |
| # OF PRIMARY LATERAL TASSEL BRANCHES | 15 | 4.40 | 1.18 | 14.40 | 0.0000 | (3.80,5.00) |
| PLANT HEIGHT(CM) | 15 | 137.3 | 8.69 | 61.19 | 0.0000 | (132.9,141.7) |
| TASSEL LENGTH(CM) | 15 | 29.87 | 3.87 | 29.89 | 0.0000 | (27.91,31.83) |
| TASSEL BRANCH ANGLE | 15 | 25.80 | 7.96 | 12.56 | 0.0000 | (21.77,29.83) |

TABLE 1-continued

ZS1783
VARIETY DESCRIPTION INFORMATION
1 Type: Dent
2 Region Best Adapted: North central from east to west

INBRED ZS1783

| | | | | | | |
|---|---|---|---|---|---|---|
| # OF TILLER PER PLANTS | 15 | 0.00 | 0.00 | | | (0.00,0.00) |
| WEIGHT PER 100 KERNELS(GM) | 15 | 22.33 | 4.14 | 20.88 | 0.0000 | (20.23,24.42) |
| EAR LENGTH(CM) | 15 | 15.10 | 0.96 | 60.92 | 0.0000 | (14.61,15.59) |
| EAR WEIGHT(GM) | 15 | 106.9 | 23.23 | 17.83 | 0.0000 | (95.17,118.7) |
| # OF KERNEL ROWS | 15 | 16.00 | 1.31 | 47.33 | 0.0000 | (15.34,16.66) |
| COB DIAMETER AT MID-POINT(MM) | 15 | 24.89 | 1.12 | 86.12 | 0.0000 | (24.32,25.45) |
| EAR DIAMETER AT MID-POINT(MM) | 15 | 39.49 | 1.65 | 92.76 | 0.0000 | (38.66,40.33) |
| KERNEL LENGTH(MM) | 15 | 9.37 | 1.04 | 34.85 | 0.0000 | (8.85,9.90) |
| KERNEL THICKNESS(MM) | 15 | 5.45 | 1.00 | 21.08 | 0.0000 | (4.95,5.96) |
| KERNEL WIDTH(MM) | 15 | 6.90 | 0.72 | 36.96 | 0.0000 | (6.53,7.27) |
| % ROUND KERNELS(SHAPE GRADE) | 15 | 50.97 | 17.71 | 11.14 | 0.0000 | (42.00,59.93) |
| SHANK LENGTH | 15 | 6.49 | 1.55 | 16.25 | 0.0000 | (5.70,7.27) |

11 DISEASE RESISTANCE -   Common corn rust = 5.5
Northern leaf blight = 1
Gray leaf spot = 5
Maize dwarf mosaic virus strain B = 9
12 The parent of ZS1783 is Holden's Inbred #148. ZS1783 has similar maturity and/or genetic background and/or phenotype as CM105, PVP #8300702, PVP #8200063 and MBS402.

The Munsell code is a reference book of color which is known and used in the industry and by persons with ordinary skill in the art of plant breeding.

The purity and homozygosity of inbred ZS1783 is constantly being tracked using isozyme genotypes as shown in Table 2.

Isozyme Genotypes for ZS1783

Isozyme data were generated for inbred corn line ZS1783 according to procedures known and published in the art. The data in Table 2 gives the electrophoresis data on ZS1783.

Table 3A compares ZS1783 to its parent Holden's Inbred #148. ZS1783 shows lower grain moisture at harvest and lower grain yield. ZS1783 is a taller inbred with higher ear placement than Holden's Inbred #148. ZS1783 reaches 10% pollination (HeatP10) and heat peek significantly later than Holden's Inbred #148. ZS1783 has less seedling vigor and significantly less seedling emergence than does Holden's Inbred #148. ZS1783 evidences more germination of plants in warm testing conditions than its parent Holden's Inbred #148.

TABLE 2

ELECTROPHORESIS RESULTS FOR ZS1783

| INBRED | ACP1 | ACP4 | ADH | MDH1 | MDH2 | PGD1 | PGD2 | PH1 | PGM | IDH2 |
|---|---|---|---|---|---|---|---|---|---|---|
| ZS1783 | 11 | 00 | 22 | 22 | 22 | 11 | 22 | 22 | 22 | 11 |

Inbred and Hybrid Performance of ZS1783

The traits and characteristics of inbred corn line ZS1783 are listed and compared with other inbreds and/or with other inbreds in hybrid combination. ZS1783 data shows important characteristics and traits. This data provides a snapshot of the inbred ZS1783.

TABLE 3A

PAIRED INBRED COMPARISON DATA

| YEAR | INBRED | VIGOR | EMERGE | PCT TILLER | PLANT HEIGHT | EAR HEIGHT | SHED | EAR QUALITY | PCT BARREN |
|---|---|---|---|---|---|---|---|---|---|
| OVERALL | ZS1783 | 3.3 | 75.8 | | 171.4 | 82.6 | 1.5 | 1.8 | |
| | Holden's Inbred#148 | 4.0 | 86.4 | | 168.3 | 69.9 | 2.0 | 2.5 | |
| | # EXPTS | 2 | 2 | | 2 | 2 | 1 | 2 | |
| | DIFF | 0.8 | 10.6 | | 3.2 | 12.7 | 0.5 | 0.8 | |
| | PROB | 0.500 | 0.067 *** | | 0.851 | 0.344 | | 0.205 | |

TABLE 3A-continued

PAIRED INBRED COMPARISON DATA

| YEAR | INBRED | HEATP10 | HEATP50 | HEATP90 | HEATS10 | HEATS50 | HEATS90 | HEATPEEK |
|---|---|---|---|---|---|---|---|---|
| OVERALL | ZS1783 | 1339 | 1355 | 1371 | 1358 | 1381 | 1417 | 1299 |
|  | Holden's Inbred#148 | 1144 | 1182 | 1229 | 1221 | 1247 | 1275 | 1073 |
|  | # EXPTS | 2 | 2 | 2 | 2 | 2 | 2 | 2 |
|  | DIFF | 195 | 173 | 142 | 136 | 134 | 142 | 226 |
|  | PROB | 0.079 *** | 0.138 | 0.222 | 0.128 | 0.125 | 0.124 | 0.095 *** |

| YEAR | INBRED | HEATBL | BL MOIST | % ROOT LODGE | % STALK LODGE | % DROPPED EARS | MOISTURE | YIELD | WARM GERM |
|---|---|---|---|---|---|---|---|---|---|
| OVERALL | ZS1783 |  |  |  |  |  | 8.9 | 33.6 | 96.5 |
|  | Holden's Inbred#148 |  |  |  |  |  | 9.5 | 56.5 | 94.8 |
|  | # EXPTS |  |  |  |  |  | 2 | 2 | 2 |
|  | DIFF |  |  |  |  |  | 0.6 | 22.9 | 1.8 |
|  | PROB |  |  |  |  |  | 0.336 |  | 0.500 |

| YEAR | INBRED | COLD GERM | % LRG ROUND | % LRG FLAT | % MED ROUND | % MED FLAT | % SML ROUND | % SML FLAT |
|---|---|---|---|---|---|---|---|---|
| OVERALL | ZS1783 | 92.3 | 13.5 | 7.0 | 67.5 | 8.2 | 3.3 | 0.4 |
|  | Holden's Inbred#148 | 94.0 | 8.1 | 10.7 | 35.7 | 37.4 | 5.1 | 2.5 |
|  | # EXPTS | 2 | 2 | 2 | 2 | 2 | 2 | 2 |
|  | DIFF | 1.8 | 5.4 | 3.7 | 31.8 | 29.2 | 1.8 | 2.1 |
|  | PROB | 0.579 | 0.349 | 0.245 | 0.110 |  |  |  |

Table 3B compares ZS1783 with CM105 and shows both inbreds yield similarly, and ZS1783 has about one point less grain moisture at harvest. ZS1783 flowers (sheds pollen and reaches silking) significantly later than does CM105. ZS1783 has similar cold germination testing results as CM105, but has slightly lower warm germination testing results. ZS1783 is a taller plant that has significantly higher ear placement than does CM105.

TABLE 3B

PAIRED INBRED COMPARISON DATA

| YEAR | INBRED | VIGOR | EMERGE | PCT TILLER | PLANT HEIGHT | EAR HEIGHT | SHED | EAR QUALITY | PCT BARREN |
|---|---|---|---|---|---|---|---|---|---|
| OVERALL | ZS1783 | 3.3 | 75.8 |  | 171.4 | 82.6 | 1.5 | 1.8 |  |
|  | CM105 | 5.3 | 93.6 |  | 146.1 | 57.8 | 1.9 | 2.5 |  |
|  | # EXPTS | 2 | 2 |  | 2 | 2 | 1 | 2 |  |
|  | DIFF | 2.0 | 17.8 |  | 25.4 | 24.8 | 0.4 | 0.8 |  |
|  | PROB | 0.156 | 0.156 |  | 0.344 | 0.081 *** |  | 0.205 |  |

| YEAR | INBRED | HEATP10 | HEATP50 | HEATP90 | HEATS10 | HEATS50 | HEATS90 |
|---|---|---|---|---|---|---|---|
| OVERALL | ZS1783 | 1339 | 1355 | 1371 | 1358 | 1381 | 1417 |
|  | CM105 | 1096 | 1122 | 1154 | 1150 | 1185 | 1211 |
|  | # EXPTS | 2 | 2 | 2 | 2 | 2 | 2 |
|  | DIFF | 243 | 234 | 217 | 208 | 196 | 206 |
|  | PROB | 0.038 ** | 0.016 ** | 0.027 ** | 0.034 ** | 0.034 ** |  |

| YEAR | INBRED | HEATPEEK | HEATBL | BL MOIST | % ROOT LODGE | % STALK LODGE | % DROPPED EARS | MOISTURE |
|---|---|---|---|---|---|---|---|---|
| OVERALL | ZS1783 | 1299 |  |  |  |  |  | 8.9 |
|  | CM105 | 1002 |  |  |  |  |  | 9.9 |
|  | # EXPTS | 2 |  |  |  |  |  | 2 |
|  | DIFF | 298 |  |  |  |  |  | 1.0 |
|  | PROB | 0.081 *** |  |  |  |  |  | 0.428 |

| YEAR | INBRED | YIELD | WARM GERM | COLD GERM | % LRG ROUND | % LRG FLAT | % MED ROUND | % MED FLAT | % SML ROUND | % SML FLAT |
|---|---|---|---|---|---|---|---|---|---|---|
| OVERALL | ZS1783 | 33.6 | 96.5 | 92.3 | 13.5 | 7.0 | 67.5 | 8.2 | 3.3 | 0.4 |
|  | CM105 | 41.0 | 98.3 | 92.3 | 5.6 | 14.0 | 34.0 | 37.5 | 4.9 | 2.8 |
|  | # EXPTS | 2 | 2 | 2 | 2 | 2 | 2 | 2 | 2 | 2 |
|  | DIFF | 7.4 | 1.8 | 0.0 | 8.0 | 7.1 | 33.5 | 29.3 | 1.6 | 2.5 |
|  | PROB |  | 0.258 |  | 0.294 | 0.172 | 0.235 |  |  |  |

Table 3C shows ZS1783 produces two bushels more yield than PVP #8300102 across four experiments and significantly lower grain harvest moisture than PVP #8300102. ZS1783 is a significantly taller plant and with significantly higher ear placement than PVP #8300102. ZS1783 flowers significantly later than PVP 8300102 and reaches heat peek significantly later. ZS1783 has better warm germination results than PVP #8300102 and significantly better cold germination results than PVP #8300102. ZS1783 has significantly lower rating on ear quality than does PVP #8300102.

TABLE 3C

PAIRED INBRED COMPARISON DATA

| YEAR | INBRED | VIGOR | EMERGE | PCT TILLER | PLANT HEIGHT | EAR HEIGHT | SHED | EAR QUALITY |
|---|---|---|---|---|---|---|---|---|
| OVERALL | ZS1783 | 3.3 | 75.8 | | 171.5 | 82.5 | 1.5 | 1.8 |
| | PVP#8300102 | 3.4 | 85.8 | | 148.9 | 64.1 | 2.0 | 2.3 |
| | # EXPTS | 4 | 4 | | 4 | 4 | 2 | 4 |
| | DIFF | 0.1 | 10.0 | | 22.5 | 18.4 | 0.5 | 0.5 |
| | PROB | 0.638 | 0.001 * | | 0.030 ** | 0.003 * | | 0.092 *** |

| YEAR | INBRED | PCT BARREN | HEATP10 | HEATP50 | HEATP90 | HEATS10 | HEATS50 |
|---|---|---|---|---|---|---|---|
| OVERALL | ZS1783 | | 1339 | 1355 | 1371 | 1358 | 1381 |
| | PVP#8300102 | | 1190 | 1222 | 1246 | 1241 | 1268 |
| | # EXPTS | | 4 | 4 | 4 | 4 | 4 |
| | DIFF | | 148 | 133 | 125 | 117 | 113 |
| | PROB | | 0.001 * | 0.001 * | 0.005 * | 0.001 * | 0.002 * |

| YEAR | INBRED | HEATS90 | HEATPEEK | HEATBL | BL MOIST | % ROOT LODGE | % STALK LODGE | % DROPPED EARS |
|---|---|---|---|---|---|---|---|---|
| OVERALL | ZS1783 | 1417 | 1299 | | | | | |
| | PCP#8300102 | 1304 | 1122 | | | | | |
| | # EXPTS | 4 | 4 | | | | | |
| | DIFF | 112 | 177 | | | | | |
| | PROB | 0.003 * | 0.001 * | | | | | |

| YEAR | INBRED | MOISTURE | YIELD | WARM GERM | COLD GERM | % LRG ROUND | % LRG FLAT | % MED ROUND |
|---|---|---|---|---|---|---|---|---|
| OVERALL | ZS1783 | 8.9 | 33.6 | 96.5 | 92.3 | 13.5 | 7.0 | 67.5 |
| | PVP#8300102 | 9.9 | 31.3 | 95.1 | 86.1 | 4.7 | 6.2 | 44.7 |
| | # EXPTS | 4 | 4 | 4 | 4 | 4 | 4 | 4 |
| | DIFF | 1.0 | 2.4 | 1.4 | 6.1 | 8.7 | 0.7 | 22.7 |
| | PROB | 0.028 ** | | 0.151 | 0.047 ** | 0.071 *** | 0.634 | 0.006 * |

| YEAR | INBRED | % MED FLAT | % SML ROUND | % SML FLAT |
|---|---|---|---|---|
| OVERALL | ZS1783 | 8.2 | 3.3 | 0.4 |
| | PVP#8300102 | 27.4 | 10.0 | 4.8 |
| | # EXPTS | 4 | 4 | 4 |
| | DIFF | 19.3 | 6.7 | 4.5 |
| | PROB | | | |

Table 3D shows ZS1783 has lower yield than PVP #8200063 and over a point less moisture of grain at harvest. ZS1783 is a taller inbred with higher ear placement than PVP #8200063. ZS1783 flowers later than PVP #8200063 and particularly reaches 10% and 50% pollination and 10% silking significantly later than PVP #8200063. ZS1783 reaches heat peek significantly later than PVP #8200063.

TABLE 3D

PAIRED INBRED COMPARISON DATA

| YEAR | INBRED | VIGOR | EMERGE | PCT TILLER | PLANT HEIGHT | EAR HEIGHT | SHED | EAR QUALITY | PCT BARREN |
|---|---|---|---|---|---|---|---|---|---|
| OVERALL | ZS1783 | 3.3 | 75.8 | | 171.4 | 82.6 | 1.5 | 1.8 | |
| | PVP#8200063 | 3.8 | 81.9 | | 161.3 | 76.2 | 1.0 | 2.8 | |
| | # EXPTS | 2 | 2 | | 2 | 2 | 1 | 2 | |
| | DIFF | 0.5 | 6.1 | | 10.2 | 6.4 | 0.5 | 1.0 | |
| | PROB | | 0.400 | | 0.156 | 0.430 | | | |

TABLE 3D-continued

PAIRED INBRED COMPARISON DATA

| YEAR | INBRED | HEATP10 | HEATP50 | HEATP90 | HEATS10 | HEATS50 | HEATS90 |
|---|---|---|---|---|---|---|---|
| OVERALL | ZS1783 | 1339 | 1355 | 1371 | 1358 | 1381 | 1417 |
|  | PVP#8200063 | 1258 | 1291 | 1318 | 1266 | 1315 | 1343 |
|  | # EXPTS | 2 | 2 | 2 | 2 | 2 | 2 |
|  | DIFF | 81 | 64 | 53 | 92 | 66 | 74 |
|  | PROB | 0.077 *** | 0.092 *** | 0.176 | 0.047 ** | 0.111 | 0.197 |

| YEAR | INBRED | HEATPEEK | HEATBL | BL MOIST | % ROOT LODGE | % STALK LODGE | % DROPPED EARS | MOISTURE |
|---|---|---|---|---|---|---|---|---|
| OVERALL | ZS1783 | 1299 |  |  |  |  |  | 8.9 |
|  | PVP#8200063 | 1212 |  |  |  |  |  | 10.3 |
|  | # EXPTS | 2 |  |  |  |  |  | 2 |
|  | DIFF | 87 |  |  |  |  |  | 1.3 |
|  | PROB | 0.026 ** |  |  |  |  |  | 0.337 |

| YEAR | INBRED | YIELD | WARM GERM | COLD GERM | % LRG ROUND | % LRG FLAT | % MED ROUND | % MED FLAT | % SML ROUND | % SML FLAT |
|---|---|---|---|---|---|---|---|---|---|---|
| OVERALL | ZS1783 | 33.6 | 96.5 | 92.3 | 13.5 | 7.0 | 67.5 | 8.2 | 3.3 | 0.4 |
|  | PVP#8200063 | 61.8 | 95.3 | 96.5 | 3.1 | 2.2 | 42.7 | 28.0 | 15.0 | 6.0 |
|  | # EXPTS | 2 | 2 | 2 | 2 | 2 | 2 | 2 | 2 | 2 |
|  | DIFF | 28.1 | 1.3 | 4.3 | 10.4 | 4.8 | 24.8 | 19.8 | 11.7 | 5.7 |
|  | PROB |  | 0.344 | 0.567 | 0.234 | 0.344 | 0.246 |  |  |  |

Table 3E compares inbred ZS1783 with MBS402. ZS1783 has lower grain moisture at harvest and lower grain yield than does MBS402. ZS1783 flowers later and reaches heat peek later than MBS402. ZS1783 has similar warm germination test results as does MBS402 but slightly lower cold germination results. ZS1783 is a slightly taller inbred than MBS402 with ear placement much higher that MBS402.

These inbred comparisons show some difference and similarities between inbreds. The additional data provided by the following tables more clearly show the uniqueness of the present invention.

TABLE 3E

PAIRED INBRED COMPARISON DATA

| YEAR | INBRED | VIGOR | EMERGE | PCT TILLER | PLANT HEIGHT | EAR HEIGHT | SHED | EAR QUALITY | PCT BARREN | HEATP10 |
|---|---|---|---|---|---|---|---|---|---|---|
| OVERALL | ZS1783 | 3.3 | 75.8 |  | 171.4 | 82.6 | 1.5 | 1.8 |  | 1339 |
|  | MBS402 | 5.3 | 94.2 |  | 168.3 | 59.7 | 1.5 | 2.5 |  | 1220 |
|  | # EXPTS | 2 | 2 |  | 2 | 2 | 1 | 2 |  | 2 |
|  | DIFF | 2.0 | 18.3 |  | 3.2 | 22.9 | 0.0 | 0.8 |  | 119 |
|  | PROB | 0.500 | 0.133 |  | 0.677 | 0.205 |  | 0.205 |  | 0.113 |

| YEAR | INBRED | HEATP50 | HEATP90 | HEATS10 | HEATS50 | HEATS90 | HEATPEEK | HEATBL | BL MOIST |
|---|---|---|---|---|---|---|---|---|---|
| OVERALL | ZS1783 | 1355 | 1371 | 1358 | 1381 | 1417 | 1299 |  |  |
|  | MBS402 | 1244 | 1261 | 1224 | 1248 | 1271 | 1153 |  |  |
|  | # EXPTS | 2 | 2 | 2 | 2 | 2 | 2 |  |  |
|  | DIFF | 112 | 110 | 134 | 133 | 145 | 146 |  |  |
|  | PROB | 0.131 | 0.107 | 0.115 | 0.105 | 0.124 | 0.163 |  |  |

| YEAR | INBRED | % ROOT LODGE | % STALK LODGE | % DROPPED EARS | MOISTURE | YIELD | WARM GERM | COLD GERM | % LRG ROUND |
|---|---|---|---|---|---|---|---|---|---|
| OVERALL | ZS1783 |  |  |  | 8.9 | 33.6 | 96.5 | 92.3 | 13.5 |
|  | MBS402 |  |  |  | 10.0 | 43.6 | 96.8 | 94.5 | 23.2 |
|  | # EXPTS |  |  |  | 2 | 2 | 2 | 2 | 2 |
|  | DIFF |  |  |  | 1.0 | 9.9 | 0.3 | 2.3 | 9.7 |
|  | PROB |  |  |  | 0.431 |  | 0.874 | 0.563 | 0.007 * |

| YEAR | INBRED | % LRG FLAT | % MED ROUND | % MED FLAT | % SML ROUND | % SML FLAT |
|---|---|---|---|---|---|---|
| OVERALL | ZS1783 | 7.0 | 67.5 | 8.2 | 3.3 | 0.4 |
|  | MBS402 | 15.5 | 47.6 | 11.2 | 2.2 | 0.3 |
|  | # EXPTS | 2 | 2 | 2 | 2 | 2 |

TABLE 3E-continued

| PAIRED INBRED COMPARISON DATA | | | | | |
|---|---|---|---|---|---|
| DIFF | | 8.6 | 19.8 | 3.0 | 1.1 | 0.1 |
| PROB | | 0.026 ** | 0.125 | | | |

Table 4 compares the resistance of ZS1783 to four common maize diseases with its parent and four comparable inbreds. ZS1783 has intermediate resistance with a 5.5 rating to common corn rust. CM105 and PVP 8200063 also have intermediate resistance with slightly lower scores. Holden's Inbred #148, PVP #8300102, MBS402evidence resistance to rust. ZS1783 has the best gray leaf spot (GLS) resistance rating at 5. The other inbreds rate at 4.5 or below for GLS. ZS1783 has been carefully bred to maintain an excellent resistance to $MDMV_B$. ZS1783 and PVP #8300102 have a 9 rating (superior) for MDMVB, CM105 has an 8 and PVP 8200063 has a 3.6. ZS1783 is susceptible to northern leaf blight.

TABLE 4

| INBRED | CCR | GLS | MDMVB | NLB |
|---|---|---|---|---|
| CM105 | 4 | 2.7 | 8 | 3.1 |
| Holden's Inbred #148 | 7 | 4.3 | . | 6.2 |
| PVP#8300102 | 6 | 2.7 | 9 | 5.5 |
| PVP#8300063 | 4.4 | 3.3 | 3.6 | 5.1 |
| MBS402 | 6.3 | 4.5 | . | 5.9 |
| ZS1783 | 5.5 | 5 | 9 | 1 |

Table 5 compares the ECBI and II resistance of ZS1783 with Holden's Inbred #148. ZS1783 has excellent resistance to first brood ECB with an 8.0 compared with Holden's Inbred #148 at a 4.0. ZS1783 has a 4.2 rating and Holden's Inbred #148 has a 4.5 rating for resistance to European Corn Borer second brood.

nation occurs. The interpretation of the data for all traits is that a positive comparison is a practical advantage. A negative comparison is a practical disadvantage. The general combining ability of an inbred is clearly evidenced by the results of the general combining ability estimates. This data compares the inbred parent in a number of hybrid combinations to a group of "checks". The check data is from other companies' hybrids, particularly the leader in the industry and ICI Seeds' commercial products and pre-commercial hybrids which were grown in the same sets and locations. ZS1783 has an advantage in its G index rating. ZS1783 shows yield by moisture (ZS1783 at 0.1, Holden's Inbred #148 at −0.7), yield (ZS1783 at −1.3, Holden's Inbred #148 at −19.6), and grain moisture at harvest (ZS1783 at 0.8, Holden's Inbred #148 at −0.4) are more positive than the same ratings for Holden's Inbred #148. ZS1783 has a 0.6 advantage in resistance to stalk lodging compared to its checks; Holden's Inbred #148 only has a 0.2 advantage in resistance to stalk lodging compared to its checks. Additionally, ZS1783 has higher advantage in resistance to root lodging and in the test weight of grain. Clearly ZS1783 performs across the board in a superior manner to Holden's Inbred #148's performance.

TABLE 6A

| | # HYBRIDS | N | YM | GI | YLD | MOIST | % SL | % RL | % DE | TWT | RM |
|---|---|---|---|---|---|---|---|---|---|---|---|
| ZS1783 | 72 | 1457 | 0.1 | 0.5 | −1.3 | 0.8 | 0.6 | 0.7 | 0.0 | 1.4 | 104 |
| Holden's Inbred #148 | 11 | 103 | −0.7 | −9.1 | −19.6 | −0.4 | 0.2 | 0.5 | 0.0 | 0.0 | 105 |

Table 6B compares ZS1783 in random hybrid combinations with CM105, PVP #8300102, PVP #8300063 and MBS402 in random hybrid combinations, each set of random hybrids being compared to checks. In each category except yield, for example, in G Index yield by moisture, moisture, % stalk lodging, % root lodging, dropped ear, and

TABLE 5

| | ECB1 | | ECB2 | | ECB TUNNELLING | |
|---|---|---|---|---|---|---|
| INBRED | VISUAL RATING | # YEARS TESTED | STANDARD RATING | # YEARS TESTED | cm OF TUNNELLING | # YEARS TESTED |
| ZS1783 | 8.0 | 2 | 4.2 | 2 | 34.0 | 2 |
| Holden's Inbred #148 | 4.0 | 2 | 4.5 | 2 | 31.7 | 2 |

Table 6A compares ZS1783 with its parent Holden's Inbred #148. Table 6A shows the GCA (general combining ability) estimates of ZS1783 compared with the GCA estimates of the other inbreds. The estimates show the general combining ability is weighted by the number of experiment/ location combinations in which the specific hybrid combitest weight of grain, ZS1783 in hybrid combination shows superior advantage over the checks. In yield ZS1783 showed superior advantage over CM105, PVP #8300102,and PVP #8300063. ZS1783 had a −1.4 rating in yield compared to MBS402's −0.7 rating. Clearly ZS1783 has the best overall complete inbred package of traits compared with these other inbreds.

TABLE 6B

|  | # HYBRIDS | N | GI | YM | YLD | MOIST | % SL | % RL | % DE | TWT | RM |
|---|---|---|---|---|---|---|---|---|---|---|---|
| ZS1783 | 72 | 1457 | 0.5 | 0.1 | −1.3 | 0.8 | 0.6 | 0.7 | 0.0 | 1.4 | 104 |
| CM105 | 16 | 191 | −8.1 | −0.8 | −14.4 | −0.4 | −1.3 | 0.5 | 0.0 | −0.8 | 88 |
| PVP#8300102 | 105 | 1486 | −2.3 | 0.0 | −3.3 | 0.5 | −0.9 | 0.1 | 0.0 | 0.5 | 90 |
| PVP#8300063 | 87 | 2446 | −1.9 | 0.0 | −2.8 | 0.5 | −0.2 | −0.3 | 0.0 | 0.6 | 105 |
| MBS402 | 117 | 8778 | −0.4 | 0.1 | −0.7 | 0.5 | −0.1 | 0.0 | 0.0 | −0.8 | 100 |

TABLE 7A

YIELD RESPONSE

| HYBRID | YIELD |
|---|---|
| ZS1783/Inbred 1 | 128 142 157 171 186 |
| Environment | 125 142 159 176 193 |

TABLE 7B

YIELD RESPONSE

| HYBRID | YIELD |
|---|---|
| ZS1783/Inbred 1 | 88 110 132 154 176 198 |
| Environment | 75 100 125 150 175 200 |

TABLE 8

1992–1994 CORN PAIRED COMPARISONS

| HYBRID | YEAR | TESTS | GI | ADV | YLD | ADV | MOIST | ADV | SL |
|---|---|---|---|---|---|---|---|---|---|
| ZS1783/CT | 92 | 10 | 181 | 2 | 162.6 | 0.1 | 27.7 | −2.9* | 0.6 |
| MBS402/CT | 92 | 10 | 179 |  | 162.5 |  | 24.7 |  | 1.7 |
| ZS1783/CT | 93 | 6 | 160 | 3 | 122.4 | −1.1 | 25.9 | 1.1 | 1.3 |
| MBS402/CT | 93 | 6 | 157 |  | 123.6 |  | 27.0 |  | 4.9 |
| ZS1783/CT | 94 | 9 | 187 | 5 | 175.0 | 4.2 | 20.1 | 1.0 | 0.6 |
| MBS402/CT | 94 | 9 | 182 |  | 170.9 |  | 21.1 |  | 2.8 |

| HYBRID | YEAR | TESTS | ADV | RL | ADV | DE | ADV | TWT | ADV |
|---|---|---|---|---|---|---|---|---|---|
| ZS1783/CT | 92 | 10 | 1.1 | 0.0 | 0.3 | 0.0 | 0.1 | 51.9 | 1.3 |
| MBS402/CT | 92 | 10 |  | 0.3 |  | 0.1 |  | 50.6 |  |
| ZS1783/CT | 93 | 6 | 3.7 | 0.0 | 0.0 | 0.0 | 0.0 | 51.6 | 1.5 |
| MBS402/CT | 93 | 6 |  | 0.0 |  | 0.0 |  | 50.0 |  |
| ZS1783/CT | 94 | 9 | 2.2 | 0.0 | 0.8 | 0.0 | 0.0 | 55.8 | 1.6 |
| MBS402/CT | 94 | 9 |  | 0.8 |  | 0.0 |  | 54.2 |  |

1993 (an unusually wet year), ZS1783 had a yield disadvantage of 1.1 compared with the MBS402/CT hybrid. In 1993 and 1994 the ZS1783 hybrid was drier than the MBS402 hybrid; in 1992 ZS1783 hybrid was significantly wetter. Across all three years the ZS1783 hybrid was equivalent to or was better than the MBS402 hybrid in resistance to stalk lodging, root lodging, and dropping ears. Additionally, the ZS1783 hybrid consistently had better grain test weight than the MBS402 hybrid. Overall the ZS1783 provides a better package of traits to the hybrid than did MBS402.

Table 7A and 7B are displayed to more clearly show the type of yield performance ZS1783 in this hybrid combination can achieve. Table 7A shows a higher yielding environment where ZS1783 in hybrid combination appears to yield well in only the lowest yield environment. Table 7B broadens the spectrum of yielding environments. Clearly ZS1783 in this hybrid combination, has excellent performance in poor yielding environments. ZS1783 is a hardy, robust inbred that can pull a hybrid's yield up in low to moderate yielding environments and supports yield in the high yielding environments.

Table 8 shows a hybrid containing ZS1783 and a common tester compared with a second hybrid containing MBS402 on the same common test across three years of testing. In all three years, the ZS1783 hybrid had a better G index rating, having advantages of 2, 3 and 5 over MBS402/CT. In 1992 and 1994 the ZS1783 hybrid had a yield advantage. In 1992 this advantage was slight, in 1994 it was four bushels in Table 9 compares a hybrid combination having ZS1783 on a common tester with 8777 which contains the common tester, and a second hybrid combination having ZS1783 on a different inbred also compared to 8777.

The ZS1783 hybrid on a common tester with 8777 (8777 is a commercially available hybrid from ICI Seeds, Coon Rapids, Iowa) shows advantages over 8777 across the board except for the grain moisture at harvest. The ZS1783/Inbred in both research plots and strip experimental trials showed across the board advantage over 8777; the single exception being a significant disadvantage in moisture in the research plots. The ZS1783 had significantly better yield than 8777 and consistently had better test weight of grain than 8777.

TABLE 9

| HYBRID | | YEAR | TESTS | GI | ADV | YLD | ADV | MOIST | ADV | SL |
|---|---|---|---|---|---|---|---|---|---|---|
| ZS1783/CT | RE | 92–94 | 25 | 178 | 3 | 157.4 | 1.3 | 24.5 | –0.5 | 0.7 |
| 8777 Having CT | RE | 92–94 | 25 | 175 | | 156.2 | | 24.0 | | 2.9 |
| ZS1783/ Inbred | RE | 92–94 | 371 | 181 | 3 | 166.1 | 2.0* | 22.0 | –0.4* | 1.8 |
| 8777 | RE | 92–94 | 371 | 178 | | 164.1 | | 21.5 | | 2.6 |
| ZS1783/ Inbred | ST | 92–94 | 145 | 182 | 3 | 163.6 | 2.5* | 19.8 | 0.1 | 1.6 |
| 8777 | ST | 92–94 | 145 | 179 | | 161.0 | | 19.9 | | 2.7 |

| HYBRID | | YEAR | TESTS | ADV | RL | ADV | DE | ADV | TWT | ADV |
|---|---|---|---|---|---|---|---|---|---|---|
| ZS1783/CT | RE | 92–94 | 25 | 2.1 | 0.0 | 0.4 | 0.0 | 0.0 | 54.2 | 1.5 |
| 8777 Having CT | RE | 92–94 | 25 | | 0.4 | | 0.0 | | 52.7 | |
| ZS1783/ Inbred | RE | 92–94 | 371 | 0.8 | 0.5 | 0.9 | 0.1 | 0.0 | 54.3 | 3.7 |
| 8777 | RE | 92–94 | 371 | | 1.4 | | 0.1 | | 50.6 | |
| ZS1783/ Inbred | ST | 92–94 | 145 | 1.1 | 0.3 | 0.8 | 0.0 | 0.1 | 57.0 | 4.4 |
| 8777 | ST | 92–94 | 145 | | 1.1 | | 0.1 | | 52.6 | |

The following conditions are met:
1. The comparison was made in at least two of the three years.
2. FIVE OR MORE 1994 STRIP TESTS/RESEARCH HAVE THE COMPARISON.
3. THE 92–94 MOIST DIFFERENCE IS BETWEEN –4 AND 4.
NOTE: The * beside the MOIST ADV and the YIELD ADV denotes significance at the .10 level.

Table 10 compares a hybrid combination of ZS1783/Inbred with ICI Seeds commercially available hybrids. A positive number indicates the ZS1783 hybrid has the advantage in that rating category over the hybrid, a negative number indicates the commercial hybrid has the advantage.

The ZS1783 hybrid has a better G index rating than does 8883. ZS1783 hybrid also has a 10 point advantage over 8883's yield. 8883 is drier and has less stalk lodging than the ZS1783 hybrid. Additionally, the ZS1783 hybrid has better test weight of grain and less root lodging than 8883.

The ZS1783 hybrid has a better yield by moisture, yield and grain moisture at harvest rating than does 8704. The ZS1783 hybrid has a lower stalk lodging rating but a better root lodging, dropped ear, and test weight for grain rating than does 8704.

The ZS1783 hybrid combination is superior in ratings in all categories when compared with 8692IT.

TABLE 10

| | | | HYBRID SUMMARY ZS1783/INBRED | | | | | | |
|---|---|---|---|---|---|---|---|---|---|
| HYBRID | | N | GI | YM | YLD | MST | % SL | % RL | % DE | TWT |
| RE 8883 | | 38 | 5.6 | –0.2 | 10.8 | –2.5 | –0.2 | 0.3 | 0.0 | 1.9 |
| RE 8704 | | 31 | 2.2 | 1.2 | 5.0 | 5.3 | –0.6 | 0.1 | 0.1 | 1.8 |
| RE 8692IT | | 38 | 3.0 | 0.9 | 4.1 | 3.5 | 0.5 | 0.5 | 0.0 | 0.9 |

This inbred is very healthy and has excellent late season integrity. The ear is long and slender with 12–14 kernel rows. The grain quality is superb. The inbred has gloss kernels. There is a slight risk if ZS1783 is used as a female in hybrid production that its tight husks may cause silk balling. The test weight of ZS1783 is heavier than most inbreds of the same region.

ZS1783 has very good general combining ability with a broad base of other inbreds. ZS1783 has strong agronomic traits like resistance to stalk lodging, root lodging, and dropping ears. ZS1783 also evidences an excellent ability to pass its high grain test weigh into the hybrid combination. ZS1783 has superb grain quality which also shows in the hybrids. ZS1783 appears to be well adapted across the central regions and makes hybrids which are likewise well adapted across this region. Additionally, ZS1783 performs well in hybrid combination and as an inbred in heat and drought stress. Overall, the inbred ZS1783 makes nice looking medium sized hybrids with excellent quality grain.

The foregoing is set forth by way of example and is not intended to limit the scope of the invention.

This invention also is directed to methods for producing a corn plant by crossing a first parent corn plant with a second parent corn plant wherein the first or second parent corn plant is an inbred corn plant from the line ZS1783. Further, both first and second parent corn plants can come from the inbred corn line ZS1783. A variety of breeding methods can be selected depending on the mode of reproduction, the trait, the condition of the germplasm. Thus, any such methods using the inbred corn line ZS1783 are part of this invention: selfing, backcrosses, hybrid production, crosses to populations, and the like.

Various culturing techniques known to those skilled in the art, such as haploid, transformation, and a host of other conventional and unconventional methods are within the scope of the invention. All plants and plant cells ,produced using inbred corn line ZS1783 are within the scope of this invention. The invention encompasses the inbred corn line used in crosses with other, different, corn inbreds to produce (F1) corn hybrid seeds and plants with the characteristics that make good hybrids. This invention includes cells which upon growth and differentiation produce corn plants having the physiological and morphological characteristics of the inbred line ZS1783.

Duncan, from at least 1985–1988 produced literature on plant regeneration from callus. Both inbred and hybrid callus have resulted in regenerated plants at excellent efficiency rates. Somatic embryogenesis has been performed on various maize tissue such as glume which before the 1980's was considered unuseable for this purpose. The prior art clearly teaches the regeneration of plants from various maize tissues.

Stauffer Chemical, the predecessor to Zeneca Ag Chem, in European Patent Application, publication 160,390, incorporated herein by reference describes tissue culture of corn. Corn tissue culture procedures are also described in the literature as early as 1982.

A deposit of at least 2500 seeds of the inbred seed of of this invention is maintained by ICI Seeds, 2369 330th Street, Slater, Iowa 50244. Access to this deposit will be available during the pendency of this application to the Commissioner of Patents and Trademarks and persons determined by the Commissioner to be entitled thereto upon request. All restrictions on availability to the public of such material are removed upon issuance of the patent. The Applicant made a deposit of at least 2500 seeds of Inbred Corn Line ZS1783 with the American Type Culture Collection (ATCC), located at 12301 Parklawn Drive, Rockville, Md. 20852. The ATCC Accession No. is 97676. The seeds were deposited with the ATCC on Aug. 8, 1996 and were taken from the inbred seed deposit maintained by ICI Seeds. The ATCC deposit will be maintained in that depository, which is a public depository, for a period of 30 years, or 5 years after the last request, or for the effective life of the patent, whichever is longer, and will be replaced if it becomes nonviable during that period. Additionally, Applicant has satisfied all the requirements of 37 C.F.R. §§1.801–1.809, including providing an indication of the viability of the sample.

Inbreds designated MBS are available from Mike Brayton Seed in Iowa. Inbreds designated SGI are available from Seed Genetic Inc. in New Jersey. Information on the ZS designations may be available from the PVP office.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:
1. Inbred corn seed designated ZS1783 seed of which has been deposited with ATCC and carry ATCC number 97676.
2. A corn plant produced by the seed of claim 1.
3. A tissue culture of regenerable cells of ZS1783 wherein the tissue regenerates plants having all the physiological and morphological characteristics of ZS1783 seed of which has been deposited with ATCC and carry ATCC number 97676.
4. A tissue culture according to claim 3, the tissue culture selected from the group consisting of leaves, pollen, embryos, roots, root tips, anthers, silk, flowers, kernels, ears, cobs, husks and stalks, and cells and protoplasts thereof.
5. A corn plant having all the physiological and morphological characteristics of ZS1783 regenerated from the tissue culture of claim 3.
6. Hybrid seed produced by:
   (a) planting, in pollinating proximity, seed of corn inbred line ZS1783, seed of which has been deposited with ATCC and carry ATCC accession number 97676, and another inbred line;
   (b) inducing the lack of pollen production by the plants of one of the inbred lines;
   (c) allowing natural cross pollination to occur between said inbred lines; and
   (d) harvesting seed produced therefrom.
7. Hybrid seed produced by hybrid combination of plants of inbred corn seed designated ZS1783 of claim 1 and plants of another inbred line.
8. Hybrid plants grown from seed of claim 7.
9. A first generation (F1) hybrid corn plant produced by the process of:
   (a) planting seed of corn inbred line ZS1783, seed of which has been deposited with ATCC and carry ATCC accession number 97676;
   (b) provide a pollen source;
   (c) inducing the lack of pollen production by the inbred line adapted to produce the hybrid seed from which hybrid seed will be harvested;
   (d) allowing pollination to occur on said inbred line adapted to produce hybrid seed;
   (e) harvesting seeds produced on plants of the inbred line of step (c); and
   (f) planting a harvested seed of step (e) to produce the F1 hybrid corn plant.
10. A tissue culture of the regenerable cells of the corn plant of claim 8.
11. A tissue culture of the regenerable cells of the corn plant of claim 9.

* * * * *